(12) United States Patent
Shimoe et al.

(10) Patent No.: US 7,211,709 B2
(45) Date of Patent: May 1, 2007

(54) DISPOSABLE WEARING ARTICLE

(75) Inventors: Nariaki Shimoe, Kagawa-ken (JP);
Toshifumi Otsubo, Kagawa-ken (JP)

(73) Assignee: Uni-Charm Co., Ltd., Ehime-ken (JP)

( * ) Notice: Subject to any disclaimer, the term of this patent is extended or adjusted under 35 U.S.C. 154(b) by 40 days.

(21) Appl. No.: 10/981,668

(22) Filed: Nov. 5, 2004

(65) Prior Publication Data

US 2005/0065490 A1    Mar. 24, 2005

Related U.S. Application Data

(63) Continuation of application No. PCT/JP03/04831, filed on Apr. 16, 2003.

(30) Foreign Application Priority Data

May 23, 2002  (JP) .............................. 2002-149581

(51) Int. Cl.
*A61F 13/514* (2006.01)
*A61F 13/537* (2006.01)

(52) U.S. Cl. .......... 604/378; 604/385.23; 604/385.101; 442/394

(58) Field of Classification Search ................ 604/367, 604/385.23, 378, 385.101; 442/14, 45, 394
See application file for complete search history.

(56) References Cited

U.S. PATENT DOCUMENTS

| | | | | |
|---|---|---|---|---|
| 2,418,907 A | * | 4/1947 | Schreiber .................... 604/359 |
| 2,682,873 A | * | 7/1954 | Evans et al. .................. 602/42 |
| 4,293,609 A | * | 10/1981 | Erickson .................... 428/201 |
| 4,306,559 A | * | 12/1981 | Nishizawa et al. .......... 604/371 |
| 4,573,986 A | * | 3/1986 | Minetola et al. ............ 604/366 |
| 4,834,735 A | * | 5/1989 | Alemany et al. ........... 604/368 |
| 4,959,059 A | * | 9/1990 | Eilender et al. ............ 604/358 |
| 5,032,120 A | * | 7/1991 | Freeland et al. ........ 604/385.27 |
| 5,143,779 A | * | 9/1992 | Newkirk et al. ............. 428/218 |
| 5,382,245 A | * | 1/1995 | Thompson et al. .......... 604/367 |
| 5,387,208 A | * | 2/1995 | Ashton et al. ............... 604/378 |
| 5,439,458 A | * | 8/1995 | Noel et al. ................... 604/378 |
| 5,460,624 A | * | 10/1995 | Ahr et al. ............... 604/385.05 |
| 5,591,151 A | * | 1/1997 | Hasse et al. ........... 604/385.25 |
| 5,704,928 A | * | 1/1998 | Morita et al. .......... 604/385.23 |

(Continued)

FOREIGN PATENT DOCUMENTS

| | | |
|---|---|---|
| EP | 0 477 802 A1 | 4/1992 |
| EP | 0 873 738 A2 | 10/1998 |
| JP | 3-16923 | 2/1991 |
| JP | 08-302568 | 11/1996 |
| JP | 2001-353181 | 12/2001 |

*Primary Examiner*—Tatyana Zalukaeva
*Assistant Examiner*—Paula L. Craig
(74) *Attorney, Agent, or Firm*—Lowe Hauptman & Berner LLP

(57) ABSTRACT

A disposable wearing article comprises a liquid-pervious topsheet, a liquid-impervious backsheet and a liquid-absorbent panel interposed between the top- and backsheets. The backsheet is formed by a breathable and hydrophobic first fibrous nonwoven fabric layer underlying the panel, a breathable and liquid-impervious plastic film underlying the first fibrous nonwoven fabric layer and a breathable and hydrophobic second fibrous nonwoven fabric layer underlying the film. In a zone occupied by the panel, the first fibrous nonwoven fabric layer is intermittently joined to an under surface of the panel by means of a hot melt adhesive and the film is intermittently joined to the first fibrous nonwoven fabric layer by means of the hot melt adhesive.

6 Claims, 10 Drawing Sheets

U.S. PATENT DOCUMENTS

| | | | |
|---|---|---|---|
| 5,783,504 A * | 7/1998 | Ehret et al. | 442/395 |
| 5,843,057 A * | 12/1998 | McCormack | 604/367 |
| 5,879,341 A * | 3/1999 | Odorzynski et al. | 604/367 |
| 5,990,376 A * | 11/1999 | Inoue et al. | 604/378 |
| 5,993,433 A * | 11/1999 | St. Louis et al. | 604/385.27 |
| 6,037,281 A * | 3/2000 | Mathis et al. | 442/394 |
| 6,049,023 A * | 4/2000 | Blenke et al. | 604/365 |
| 6,075,179 A * | 6/2000 | McCormack et al. | 604/367 |
| 6,114,596 A * | 9/2000 | Nayak et al. | 604/370 |
| 6,120,487 A * | 9/2000 | Ashton | 604/385.29 |
| 6,198,018 B1 * | 3/2001 | Curro | 604/367 |
| 6,258,996 B1 * | 7/2001 | Goldman | 604/368 |
| 6,413,247 B1 * | 7/2002 | Carlucci et al. | 604/385.01 |
| 6,613,955 B1 * | 9/2003 | Lindsay et al. | 604/378 |
| 6,623,464 B2 * | 9/2003 | Bewick-Sonntag et al. | 604/385.03 |
| 6,635,798 B1 * | 10/2003 | Yoshioka et al. | 604/365 |
| 6,663,611 B2 * | 12/2003 | Blaney et al. | 604/385.01 |
| 7,122,023 B1 * | 10/2006 | Hinoki | 604/385.101 |
| 2002/0087140 A1 * | 7/2002 | Otsubo | 604/385.28 |
| 2002/0106959 A1 * | 8/2002 | Huffines et al. | 442/394 |
| 2003/0097105 A1 * | 5/2003 | Chen et al. | 604/378 |

\* cited by examiner

DISPOSABLE WEARING ARTICLE

This application is a continuation of International Application No. PCT/JP03/04831 filed Apr. 16, 2003, which claims priority to Japanese Application No. 2002-149581 filed May 23, 2002, all of which are hereby incorporated by reference herein in their entirety.

BACKGROUND OF THE INVENTION

This invention relates to a disposable wearing article adapted to absorption and to containment of bodily discharges.

Conventional disposable wearing articles comprise a liquid-pervious topsheet facing a wearer's body, a liquid-impervious backsheet facing away from the wearer's body, a liquid-absorbent panel interposed between these top- and backsheet, a pair of end flaps extending outside longitudinally opposite ends of the panel and a pair of side flaps extending outside transversely opposite side edges of the panel and are composed of a front waist region, a rear waist region and a crotch region extending between these waist regions.

The conventional wearing article as has been described above will be described more in details in reference to FIGS. 8–10 of the accompanying drawings. FIG. 8 is a partially cutaway developed plan view showing the article 1C as its front and rear waist regions 23, 25 disconnected from each other. FIGS. 9 and 10 are sectional views taken along lines E—E and F—F, respectively, in FIG. 8, showing the article 1C being slightly curved. In FIG. 8, a waist-circumferential direction is indicated by an arrow X and a longitudinal direction is indicated by an arrow Y. This article 1C is so-called pull-on disposable diaper and actually placed on the market in the trade name of REHABILI-PANTS (supplied from Uni-Charm Corporation).

The article 1C comprises a liquid-pervious topsheet 20, a substantially liquid-impervious backsheet 21 and a liquid-absorbent panel 22 interposed between these top- and backsheets 20, 21. The article 1C has front and rear waist regions 23, 25, a crotch region 24 extending between the waist regions 23, 25, a pair of end flaps 26 and a pair of side flaps 27. While it is not shown, the side flaps 27 of the front and rear waist regions 23, 25 are overlaid and joined together by means of a plurality of welding lines 28 arranged intermittently in the longitudinal direction.

The topsheet 20 is made of a hydrophilic fibrous nonwoven fabric f6 and slightly larger than an upper surface of the panel 22, entirely covering the upper surface of the panel 22. The topsheet 20 has its inner surface intermittently joined to the upper surface of the panel 22 by means of an adhesive g.

The backsheet 21 comprises a breathable but liquid-impervious plastic film f7, a breathable but hydrophobic first fibrous nonwoven fabric layer f8 under the film f7 and a breathable but hydrophobic second fibrous nonwoven fabric layer f9 underlying the first fibrous nonwoven fabric layer f8. The film f7 is larger than the panel 22 and covers an entire under surface of the panel 22. The first and second fibrous nonwoven fabric layers f8, f9 are respectively larger than the film f7 and cover an entire under surface of the panel 22. Portions of these first and second fibrous nonwoven fabric layers f8, f9 extending outward beyond longitudinally opposite ends and transversely opposite side edges of the panel 22 define the end flaps 26 and the side flaps 27. The panel 22 is a mixture of fluff pulp and super-absorbent polymer particles or a mixture of fluff pulp, super-absorbent polymer particles and thermoplastic synthetic resin fibers, in any case, compressed to a desired thickness.

In a zone where the panel 22 is present, the film f7 has its inner surface intermittently joined to the lower surface of the panel 22 by means of the adhesive g and its outer surface intermittently joined to an inner surface of the first fibrous nonwoven fabric layer f8 by means of the adhesive g. The first and second fibrous nonwoven fabric layers f8, f9 are not joined in the zone where the panel 22 is present but intermittently joined in the end flaps 26 and the side flaps 27 by means of the adhesive g. The topsheet 20 and the first fibrous nonwoven fabric layer f8 are intermittently joined in the end flaps 26 and the side flaps 27 by means of the adhesive g. A hot melt adhesive is used as the adhesive g for the article 1C.

The breathable but liquid-impervious film f7 joined to the under surface of the panel 22 prevents any amount of body discharges such as urine, moisture contained in feces or menstrual discharge having been absorbed by the panel 22 from permeating the first and second fibrous nonwoven fabric layers f8, f9 and, in addition, prevents the panel 22 from getting out of its initial shape in the article 1C.

Based on a series of measurement conducted on this article 1C, it has been found that a vapor permeability of 2113 g/m$^2$·24 hrs is obtained when the film f7 is coated with 5 g/m$^2$ of the adhesive g in the zone where the panel 22 is present and a vapor permeability of 1983 g/m$^2$·24 hrs is obtained when the film f7 is coated with 10 g/m$^2$ of the adhesive g. Measurement of the vapor permeability is subjected to the article 1C without the topsheet in the thickness direction of the article 1C in the zone where the panel 22 is present.

While this article 1C may probably prevent any significant amount of body discharges from permeating the first and second fibrous nonwoven fabric layers f8, f9, the adhesive g by means of which the film f7 is joined to the panel 22 and the first fibrous nonwoven fabric layer f8 deteriorates the vapor permeability of the film f7 and the permeability of the article 1C in the zone where the panel 22 is present. With the article 1C put on a wearer's body, it is difficult to let out vapor from the interior to the exterior of the article 1C and thereby to protect the wearer from uncomfortable stuffiness possibly generated within the article 1C.

SUMMARY OF THE INVENTION

It is an object of this invention to provide a disposable wearing article having a capability to prevent leakage of body discharge and a sufficiently high vapor permeability to prevent stuffiness possibly generated within the article put on a wearer's body.

According to this invention, there is provided a disposable wearing article comprising a liquid-pervious topsheet facing a wearer's body, a liquid-impervious backsheet facing away from the wearer's body, a liquid-absorbent panel interposed between these top- and backsheets, a pair of end flaps extending outside longitudinally opposite ends of the panel and a pair of side flaps extending outside transversely opposite side edges of the panel.

The disposable wearing article according to this invention further comprises the backsheet formed by a breathable but hydrophobic first fibrous nonwoven fabric layer underlying the panel and covering at least an entire under surface of the panel, a breathable but liquid-impervious plastic film underlying the first fibrous nonwoven fabric and covering at least the entire under surface of the panel, and a breathable but hydrophobic second fibrous nonwoven fabric layer underlying the film and being sufficiently larger than the film so as to cover the entire under surface of the panel. In a zone occupied by the panel, the first fibrous nonwoven fabric layer is intermittently bonded to the under surface of the panel by means of a hot melt adhesive and the film is intermittently bonded to the first fibrous nonwoven fabric layer or the second fibrous nonwoven fabric layer by means of the adhesive.

This invention includes the following embodiments. The article without the topsheet exhibits a vapor-permeability in a thickness direction of 2000–3800 g/m²·24 hrs as measured in the zone occupied by the panel.

An amount of the adhesive with which the first fibrous nonwoven fabric layer and the film are coated is in a range of 1–10 g/m² as measured in the zone occupied by the panel.

Major parts of the end flaps and the side flaps are defined by the first and second fibrous nonwoven fabric flayers and the film, at least by the second fibrous nonwoven fabric layer. In the end flaps and the side flaps, the topsheet is intermittently joined to the first and second fibrous nonwoven fabric layer, at least to the first fibrous nonwoven fabric layer, and the first fibrous nonwoven fabric layer and the second fibrous nonwoven fabric layer are intermittently joined together.

The topsheet is made of a breathable and hydrophilic fibrous nonwoven fabric and intermittently joined to an upper surface of the panel by means of the adhesive.

The article is composed of front and rear waist regions opposed to each other and a crotch region extending between the waist regions and the side flaps in the front and rear waist regions are connected together so as to define a waist-hole and a pair of leg-holes.

DETAILED DESCRIPTION OF THE PREFERRED EMBODIMENTS

Details of the disposable wearing article according to this invention will be more fully understood from the description given hereunder in reference with the accompanying drawings.

Figure 1:
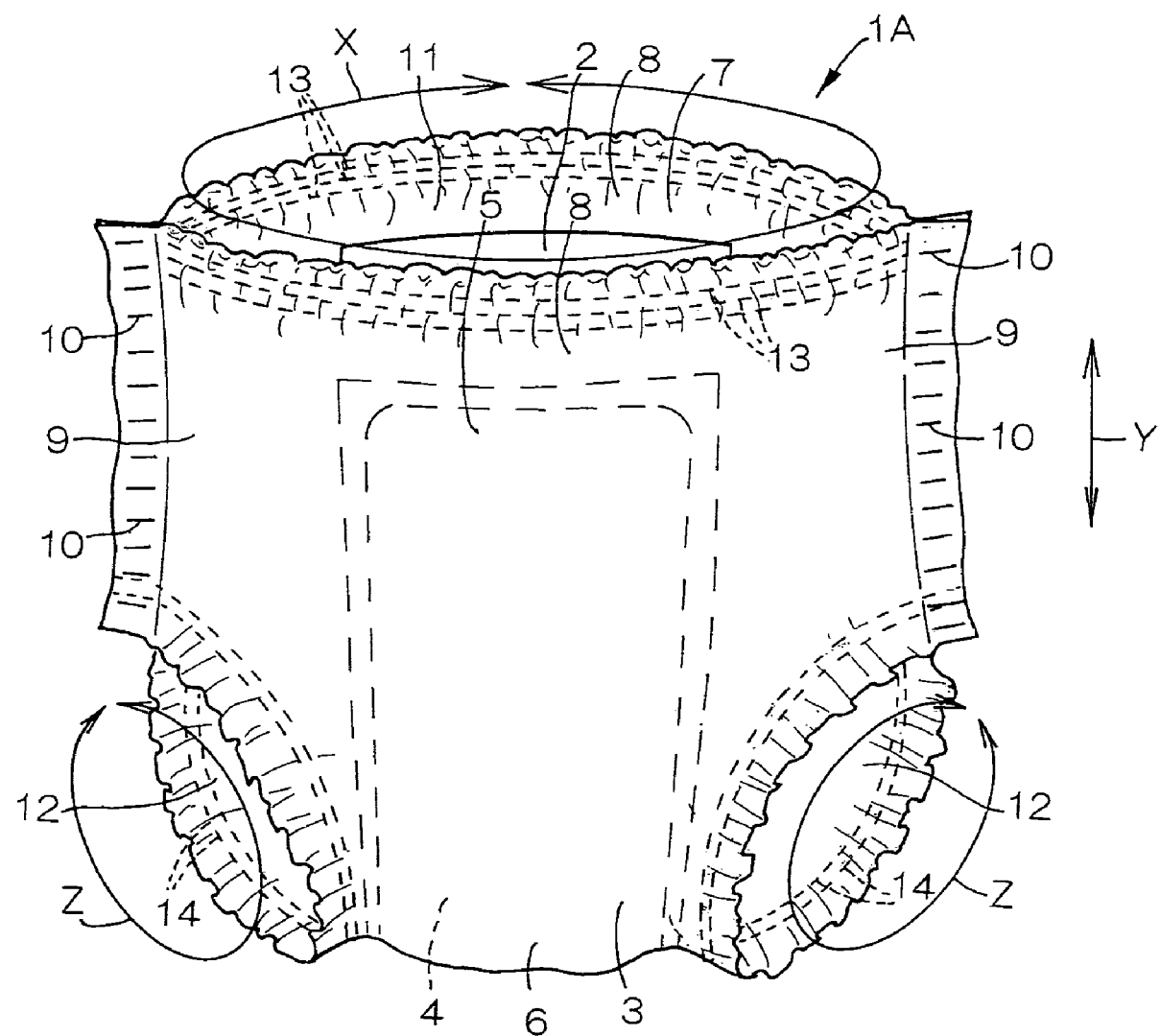
FIG. 1 is a partially cutaway perspective view showing a specific embodiment of the article according to this invention.
Figure 2:
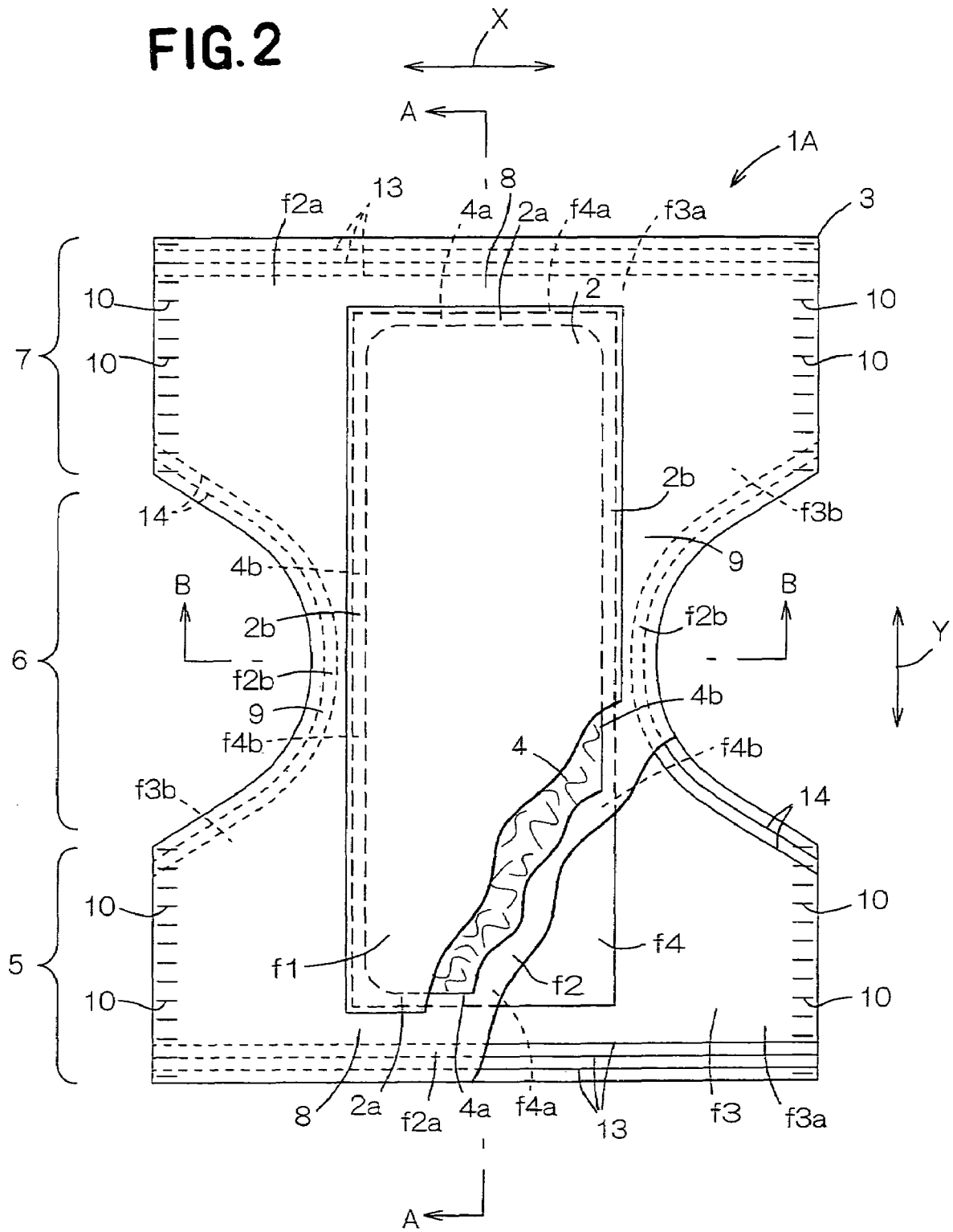
FIG. 2 is a partially cutaway developed plan view showing the article of FIG. 1 as its front and rear waist regions disconnected from each other.
Figure 3:
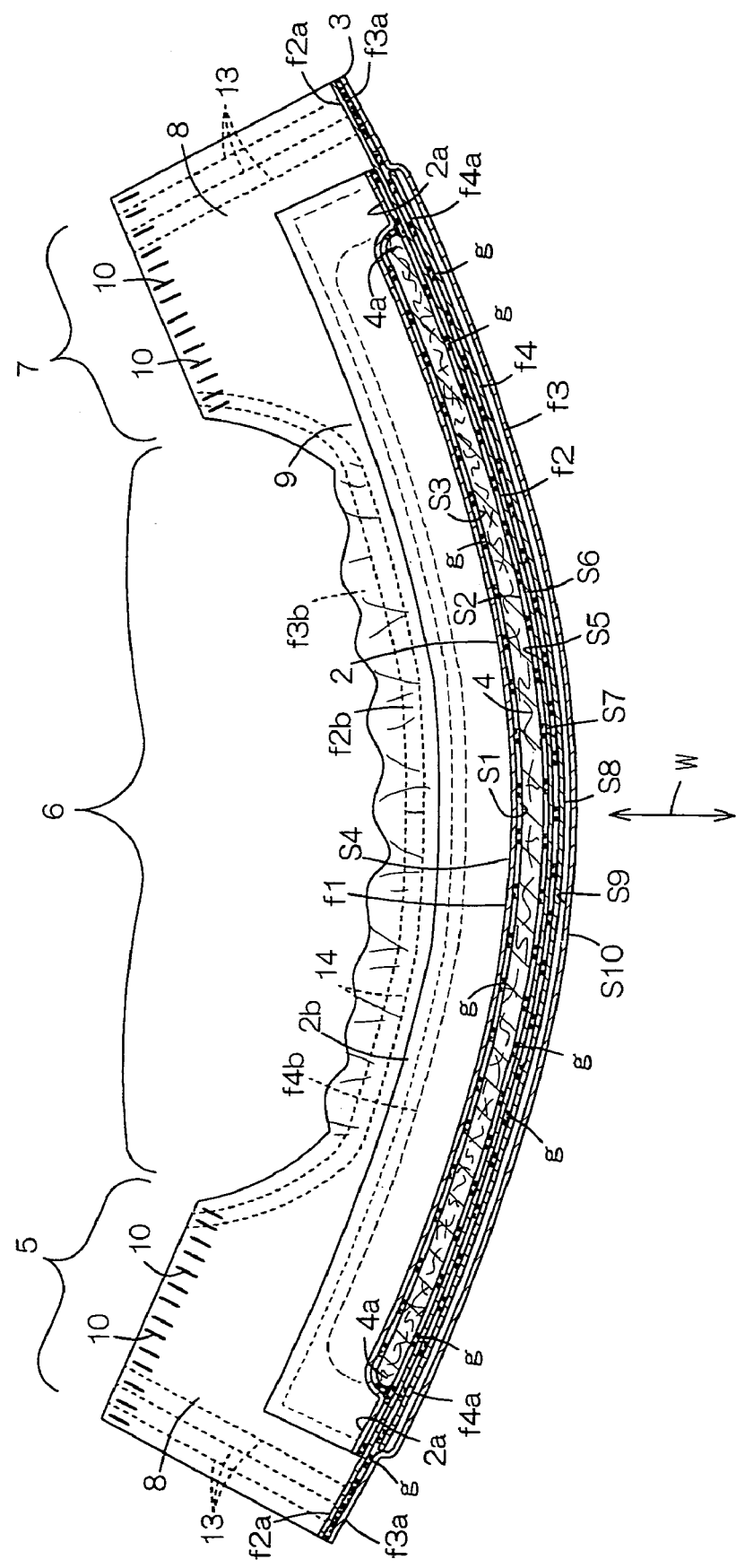
FIG. 3 is a sectional view taken along a line A—A in FIG. 2.
Figure 4:
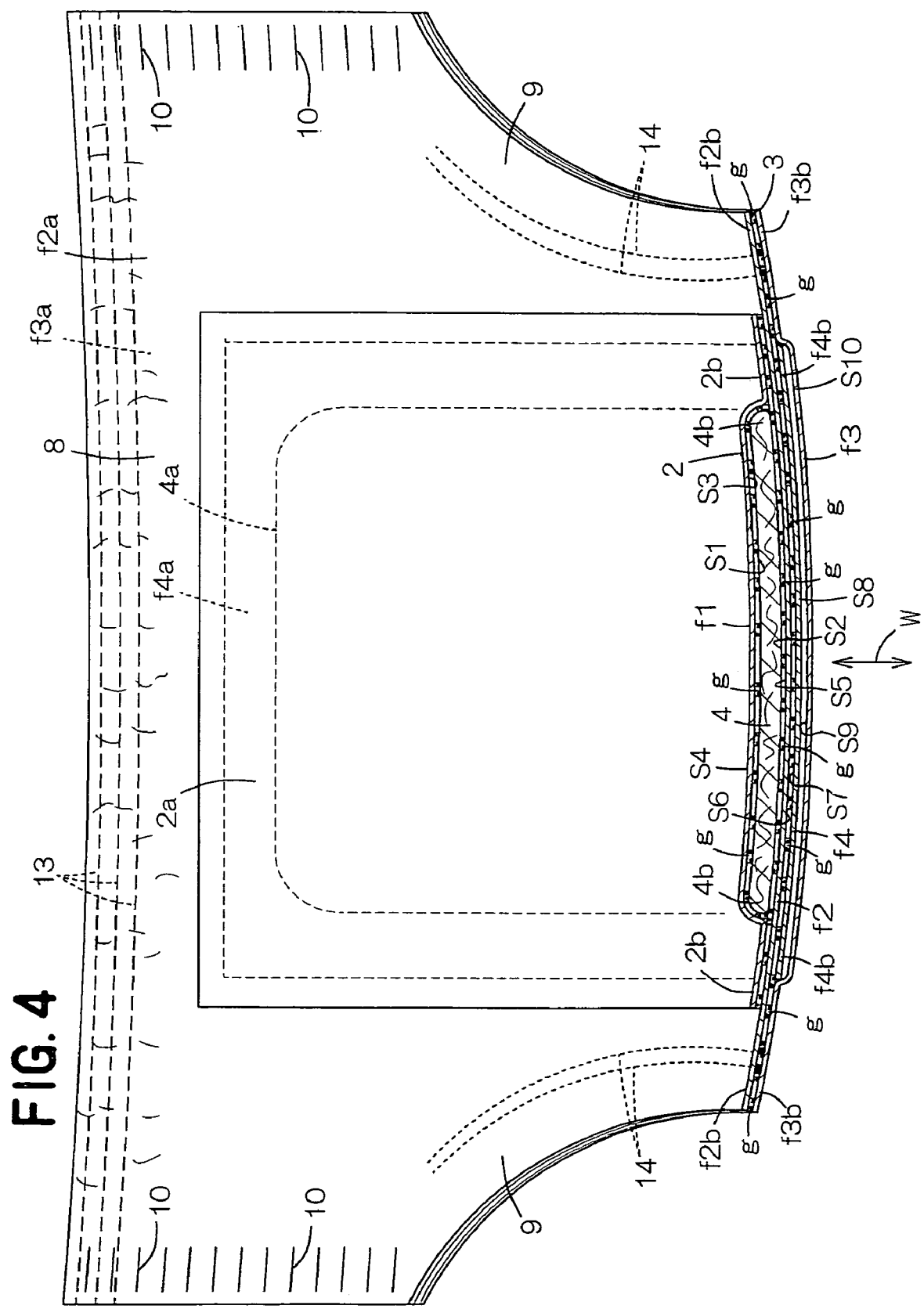
FIG. 4 is a sectional view taken along a line B—B in FIG. 2.

FIG. 1 is a partially cutaway perspective view showing a specific embodiment 1A of the article according to this invention and FIG. 2 is a developed plan view showing the article 1A of FIG. 1 as its front and rear waist regions 5, 7 disconnected from each other. FIG. 3 is a sectional view taken along a line A—A in FIG. 2 and FIG. 4 is a sectional view taken along a line B—B in FIG. 2. In FIGS. 1 and 2, a waist-circumferential direction is indicated by an arrow X, a longitudinal direction is indicated by an arrow Y and a leg-circumferential direction is indicated by an arrow Z (the arrow Z is indicated in FIG. 1 alone). In FIGS. 3 and 4, a thickness direction is indicated by an arrow W.

The expression used herein "an upper surface S1 of the panel 4" should be understood to be a surface facing a wearer's body and the expression used herein "an under surface S2" should be understood to be a surface facing away from the wearer's body. The expression used herein "inner surfaces S3, S5, S7, S9 of the topsheet 3, the first and second fibrous nonwoven fabric layers f2, f3 forming the backsheet 3, and the plastic film f4, respectively, should be understood to be surfaces facing the panel 4 and the expression used herein "outer surfaces S4, S6, S8, S10 thereof" should be understood to be the surfaces facing away from the panel 4.

The article 1A comprises a liquid-pervious topsheet 2 facing a wearer's body, a substantially liquid-impervious backsheet 3 facing away from the wearer's body and a liquid-absorbent panel 4 interposed between the top- and backsheets 2, 3. The article 1A is composed of a front waist region 5 and a rear waist region 7 opposed to each other, and a crotch region 6 extending between the waist regions 5, 7.

The article 1A has a pair of end flaps 8 extending outside longitudinally opposite ends 4a of the panel 4 and a pair of side flaps 9 extending outside transversely opposite side edges 4b of the panel 4. The end flaps 8 extend in the front and rear waist regions 5, 7 in a waist-circumferential direction. The side flaps 9 extend in the longitudinal direction between the end flaps 8 as well as in a leg-circumferential direction. In the crotch region 6, the side flaps 9 curve inward in the waist-circumferential direction of the article 1A so as to describe circular arcs, as best seen in FIG. 2. The article 1A thus presents a substantially hourglass-like planar shape.

In the article 1A, the side flaps 9 of the front and rear waist regions 5, 7 are overlaid and joined together by means of a plurality of welding lines 10 arranged intermittently in the longitudinal direction. The article 1A is of pull-on and has a waist-hole 11 and a pair of leg-holes 12.

The end flaps 8 are respectively provided with a plurality of waist elastic members 13 extending in the waist-circumferential direction and contractibly attached thereto. In the crotch region 6, the side flaps 9 are respectively provided with a plurality of leg elastic members 14 extending in the leg-circumferential direction and contractibly attached thereto.

The panel 4 extends over the crotch region 6 into the front and rear waist regions 5, 7. The panel 4 is a mixture of fluff pulp and super-absorbent polymer particles or a mixture of fluff pulp, super-absorbent polymer particles and thermoplastic synthetic resin fibers, in any case, compressed to a desired thickness. The panel 4 is preferably covered entirely with a liquid-pervious sheet made of, for example, a tissue paper or a hydrophilic fibrous nonwoven fabric in order to avoid falling-off of the polymer particles from the panel 4.

The topsheet 2 is made of a breathable hydrophilic fibrous nonwoven fabric f1. The topsheet 2 is slightly larger than an upper surface S1 of the panel 4 so as to cover the entire upper surface S1. The topsheet 2 has longitudinally opposite margins 2a extending outward beyond the longitudinally opposite ends 4a of the panel 4 and transversely opposite margins 2b extending outward beyond the transversely opposite side edges 4b of the panel 4. The topsheet 2 has its inner surface S3 intermittently joined to the upper surface S1 of the panel 4 by means of a hot melt adhesive g with which the inner surface S3 is coated.

The backsheet 3 comprises a breathable but hydrophobic first fibrous nonwoven fabric layer f2, a breathable hydrophobic second fibrous nonwoven fabric layer f3 and a breathable but liquid-impervious plastic film f4. In the backsheet 3, the first fibrous nonwoven fabric layer f2 underlies the panel 4, the film f4 underlies the first fibrous nonwoven fabric layer f2 and the second fibrous nonwoven fabric layer f3 underlies the film f4.

The first and second fibrous nonwoven fabric layers f2, f3 respectively are larger than the film f4 and cover an entire under surface S2 of the panel 4. The film f4 is slightly larger than the under surface S2 of the panel 4 and covers the entire under surface S2 of the panel 4. The first and second fibrous nonwoven fabric layers f2, f3 and the film f4 respectively have longitudinally opposite margins f2a, f3a, f4a extending outside the longitudinally opposite ends 4a of the panel 4 and transversely opposite margins f2b, f3b, f4b extending outside the transversely opposite side edges 4b of the panel 4. The end flaps 8 are substantially defined by the longitudinally opposite margins f2a, f3a of the first and second fibrous nonwoven fabric layers f2, f3, respectively. The side flaps 9 are substantially defined by the transversely opposite margins f2b, f3b of the first and second fibrous nonwoven fabric layers f2, f3, respectively.

In the zone where the panel 4 is present, the first fibrous nonwoven fabric layer f2 has its inner surface S5 intermittently joined to the under surface S2 of the panel 4 by means of the hot melt adhesive g with which the first fibrous nonwoven fabric layer f2 is coated and the film f4 has its inner surface S7 intermittently joined to an outer surface S6 of the first fibrous nonwoven fabric layer f2 by means of the hot melt adhesive g with which the film f4 is coated. In the zone where the panel 4 is present, the film f4 has its outer surface S8 is not bonded to an inner surface S9 of the second fibrous nonwoven fabric layer f3. In this zone where the panel 4 is present, the adhesive g is intermittently applied substantially over whole areas of the inner surface S3 of the topsheet 2, the inner surface S5 of the nonwoven fabric layer f2 and the inner surface S7 of the film f4.

In the end flaps 8, the longitudinally opposite margins 2a of the top sheet 2 as well as the longitudinally opposite margins f4a of the film f4 extend outward slightly beyond the longitudinally opposite ends 4a of the panel 4 in the longitudinal direction and the longitudinally opposite margins f2a, f3a of the first and second fibrous nonwoven fabric layers f2, f3, respectively, extend further outward beyond the longitudinally opposite margins 2a, f4a in the longitudinal direction, as will be apparent from FIG. 3.

Along the longitudinally opposite margins 2a and the longitudinally opposite margins f2a, the respective inner surfaces S3, S5 of the topsheet 2 and the first fibrous nonwoven fabric layer f2 are intermittently joined by means of the hot melt adhesive g. Along the longitudinally opposite margins f2a and the longitudinally opposite margins f4a, the outer surface S6 of the first fibrous nonwoven fabric layer f2 and the inner surface S7 of the film f4 are intermittently joined by means of the hot melt adhesive g. Along the longitudinally opposite margins f2a and the longitudinally opposite margins f3a, the outer surface S6 of the first fibrous nonwoven fabric layer f2 and the inner surface S9 of the second fibrous nonwoven fabric layer f3 are intermittently joined by means of the hot melt adhesive g.

The waist elastic members 13 are interposed between the longitudinally opposite margins f2a of the first fibrous nonwoven fabric layer f2 and the longitudinally opposite margins f3a of the second fibrous nonwoven fabric layer f3 and joined to the inner and outer surfaces S6, S9 of the nonwoven fabric layers f2, f3, respectively.

In the side flaps 9, the transversely opposite margins 2b of the topsheet 2 and the transversely opposite margins f4b of the film f4 extend outward slightly beyond the transversely opposite side edges 4b of the panel 4 in the waist-circumferential direction and the transversely opposite margins f2b, f3b of the first and second fibrous nonwoven fabric layers f2, f3, respectively, extend further outward beyond the transversely opposite margins 2b, f4b in the waist-circumferential direction, as best seen in FIG. 4.

Along the transversely opposite margins 2b and the transversely opposite margins f2b, the topsheet 2 and the first fibrous nonwoven fabric layer f2 respectively have the inner surfaces S3, S5 intermittently joined together by means of the hot melt adhesive g. Along the transversely opposite margins f2b and the transversely opposite margins f4b, the first fibrous nonwoven fabric layer f2 and the film f4 respectively have the outer surface S6 and the inner surface S7 intermittently joined together by means of the hot melt adhesive g. Along the transversely opposite margins f2b and the transversely opposite margins f3b, the first fibrous nonwoven fabric layer f2 and the second fibrous nonwoven fabric layer f3 respectively have the outer surface S6 and the inner surface S9 intermittently joined together by means of the hot melt adhesive g.

The leg elastic members 14 are interposed between the transversely opposite margins f2b of the first fibrous nonwoven fabric layer f2 and the transversely opposite margins f3b of the second fibrous nonwoven fabric layer f3 and joined to the inner surface S6 and the outer surface S9 of these nonwovenfabric layers f2, f3, respectively.

The article 1A presents its vapor-permeability in a range of 2000–3800 g/m$^2$·24 hrs. This vapor-permeability is the value as measured in the thickness direction of the article 1A without the topsheet 2 in the zone where the panel 4 is present, i.e., the vapor-permeability in the thickness direction of the laminate comprising the panel 4, the first and second fibrous nonwoven fabric layers f2, f3 and the film f4.

The vapor-permeability of the article 1A as well as the vapor-permeability of the conventional article 1C was measured using the following method.

(1) A plurality of cylindrical cups each having a radius of 3 cm (diameter of 6 cm) (those similar to the vapor-permeable cup used in accordance with JIS Z-0208) were prepared and 20 cc of water was poured into each of these cups.

(2) A plurality of circular test sample pieces each having a diameter 1 cm larger than that of the cup were prepared and a top opening of the cup was closed with each of the test sample pieces (in accordance with JIS Z-0208). This test sample piece was the above-described laminate of the panel 4, the first and second fibrous nonwoven fabric layers f2, f3 and the film f4.

(3) The cup was sealed with a sealing wax so that no gap might be left between the outer peripheral surface of the cup and the test sample piece (sealing method using the sealing wax was specified by JIS Z-0208).

(4) The cup carrying the test sample piece was placed within a thermo-hygrostat regulated at a temperature of 20° C. ±0.5° C. and a relative humidity of 60% ±2% and the cup was taken out from the thermo-hygrostat after 24 hours have elapsed whereupon a weight of the cup (weight A) was measured.

(5) The cup carrying the test sample piece was placed again within the thermo-hygrostat regulated at a temperature of 40° C. ±0.5° C. and a relative humidity of 60% ±2% and the cup was taken out from the thermo-hygrostat after 24 hours have elapsed whereupon a weight of the cup (weight B) was measured. The thermo-hygrostat used herein was specified by JIS Z-0208.

(6) Values of the vapor-permeability were calculated for the individual test sample pieces according to an equation as will be indicated and then an average vapor-permeability was calculated from those values for the individual test sample pieces. The average vapor-permeability of these test pieces was used as the vapor-permeability of the respective articles 1A, 1C in the thickness direction thereof in the respective regions where the panels 4, 22 were present.

Calculation of the vapor-permeability for the individual test sample pieces is based on the equation:

$$\text{Vapor-permeability}(g/m^2 \cdot 24\text{hrs}) = (\text{weight } B - \text{weight } A)/(\pi \times 0.03^2).$$

If the vapor-permeability is less than 2000 g/m²·24 hrs, it will be difficult to let moisture vapor out from the interior to the exterior of the article 1A and consequently to prevent the interior of the article 1A from become stuffy.

In the zone where the panel 4 is present, an amount of the adhesive with which the first fibrous nonwoven fabric layer f2 and the film f4 are coated is in a range of 1–10 g/m². If the coating quantity of the adhesive g is less than 1 g/m², it will be certainly effective to improve the vapor-permeability of the article 1A but it will be likely that the first fibrous nonwoven fabric layer f2 might be peeled off from the panel 4 and/or the film f4 might be peeled off from the first fibrous nonwoven fabric layer f2 due to weakness of the joining effect by the adhesive g. If the coating amount of the adhesive g exceeds 10 g/m² on the contrary, such excessive amount of the adhesive g will deteriorate the vapor-permeability of the first fibrous nonwoven fabric layer f2 and/or the film f4, eventually of the article 1A as a whole, and make it difficult to achieve the desired vapor-permeability of 2000 g/m²·24 hrs or higher.

The adhesive g may be applied on the topsheet 2, the first and second fibrous nonwoven fabric layers f2, f3 and the film f4 in a pattern selected from spiral-, zigzag-, dot- and stripe-patterns. These coating patterns result in defining adhesive coated areas and adhesive-free areas on the topsheet 2, the first and second fibrous nonwoven fabric layers f2, f3, and the film f4.

In the article 1A, the film f4 presents a vapor-permeability in a range of 2150–4000 g/m²·24 hrs. If the vapor-permeability of the film f4 is less than 2150 g/m²·24 hrs, it will be impossible to achieve the desired vapor-permeability of the article 1A as a whole in a range of 2000 g/m²·24 hrs or higher. If the vapor-permeability of the film f4 exceeds 4000 g/m²·24 hrs, there will be an anxiety that body discharges such as urine or moisture contained in feces or menstrual discharge might exudates through the adhesive-free areas. If the vapor-permeability of the film f4 is 4000 g/m²·24 hrs or less and the adhesive coating amount is 1 g/m², the vapor-permeability of the article 1A as a whole will be 3800 g/m²·24 hrs or less. Even in this case, the vapor-permeability of the article 1A as a whole can be maintained higher than the conventional article 1C.

In the article 1A, a basis weight of the topsheet 2, the first and second fibrous nonwoven fabric layers f2, f3 and the film f4 is in a range of 15–40 g/m². If the basis weight of these topsheet 2, first and second fibrous nonwoven fabric layers f2, f3 and film f4 is less than 15 g/m², a strength of the components will be deteriorate and the first and second fibrous nonwoven fabric layers f2, f3 and the film f4 will be apt to be damaged. The basis weight of the first and second fibrous nonwoven fabric layers f2, f3 and the film f4 exceeds 40 g/m², the backsheet 3 will become relatively stiff and its flexibility will be deteriorated.

Figure 8:
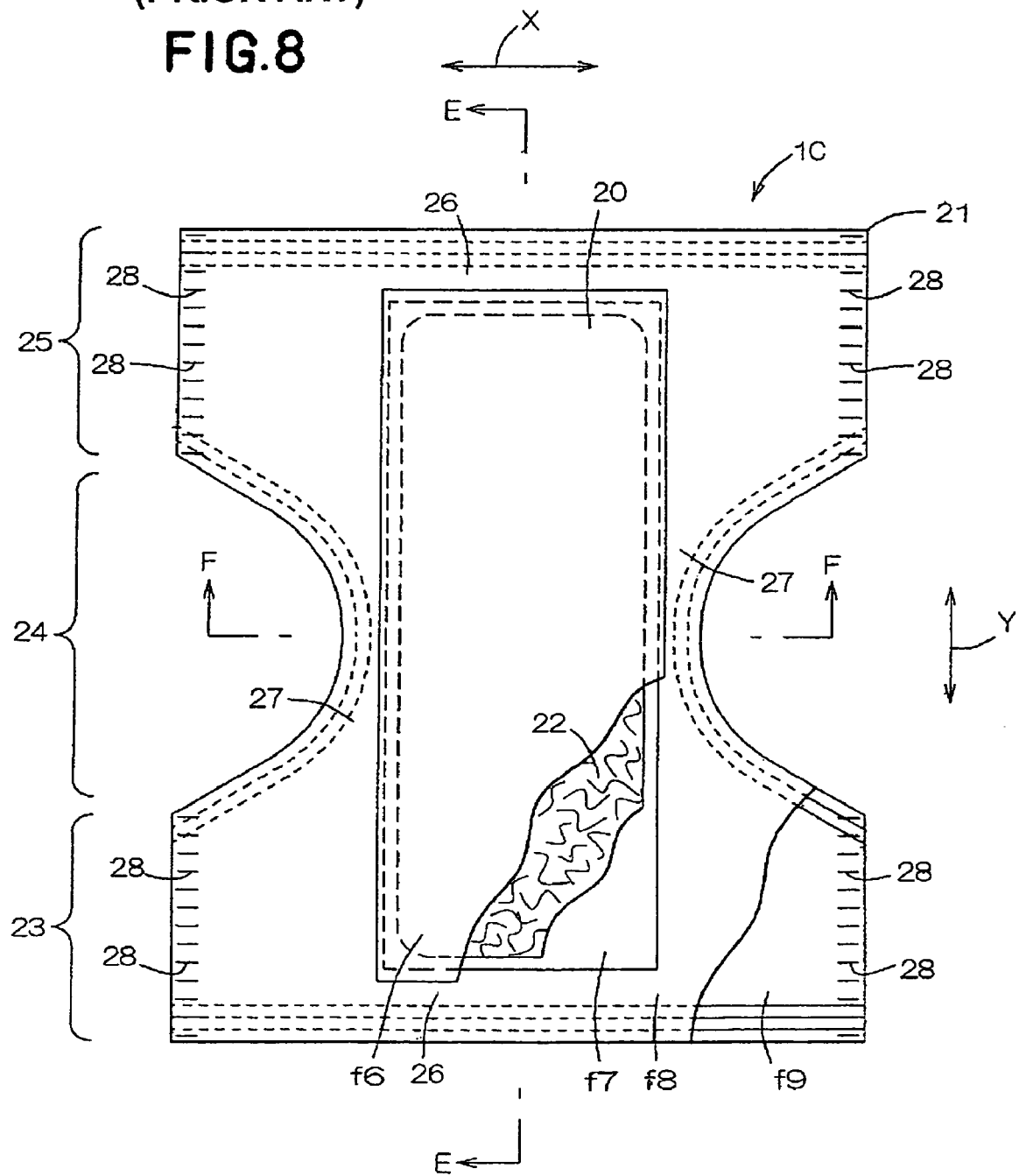
FIG. 8 is a partially cutaway developed plan view showing the conventional article as its front and rear waist regions disconnected from each other.
Figure 9:
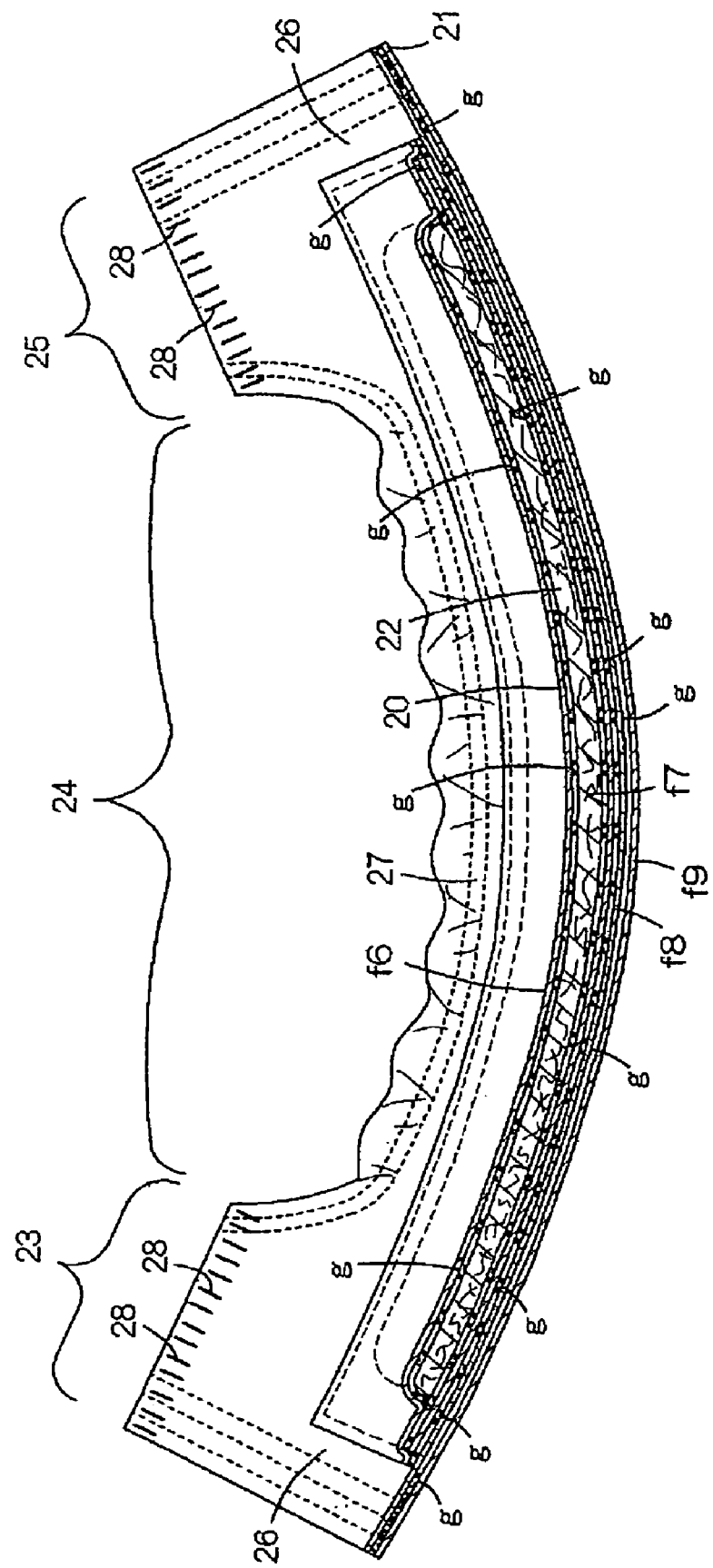
FIG. 9 is a sectional view taken along a line E—E in FIG. 8.
Figure 10:
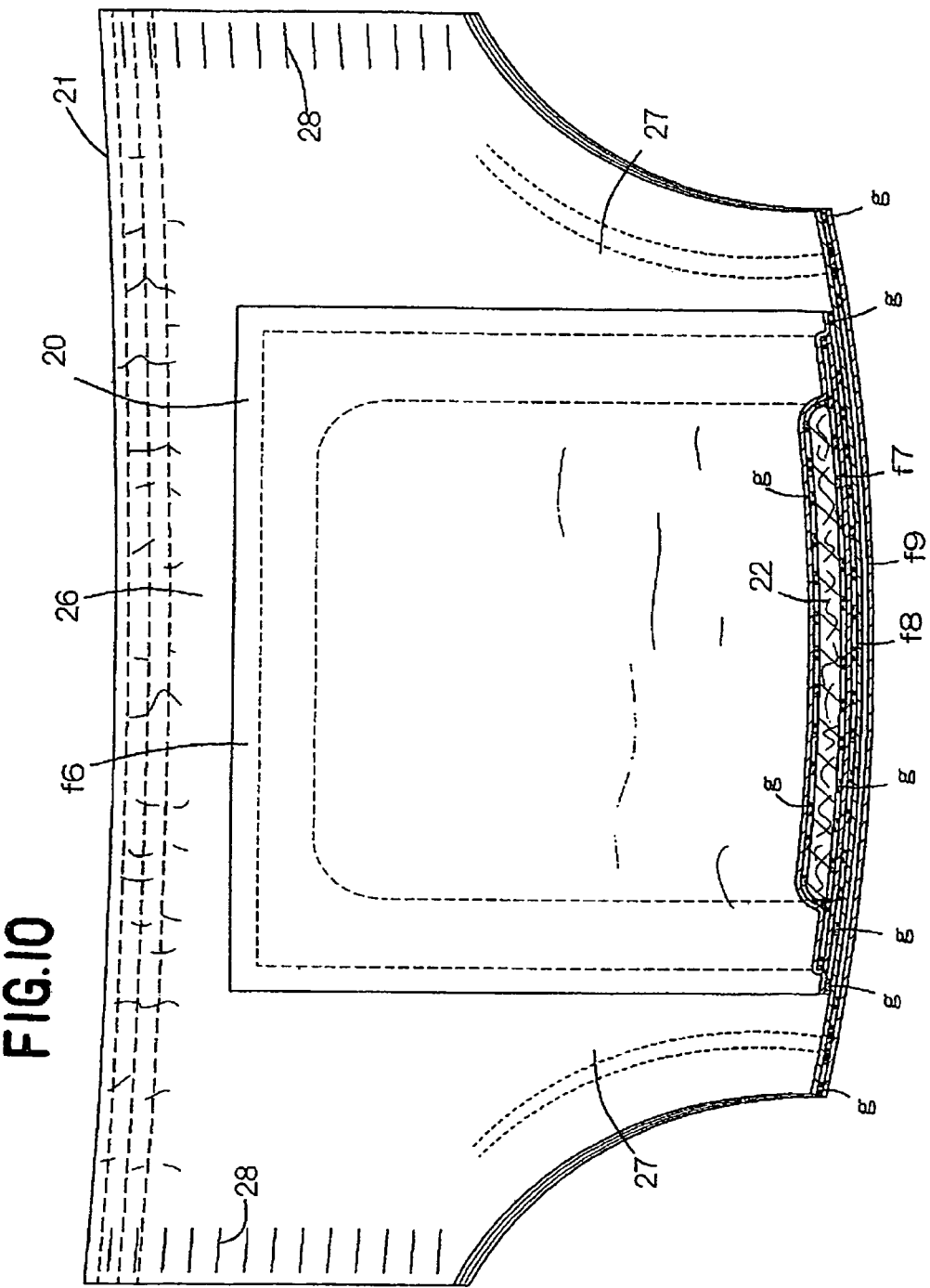
FIG. 10 is a sectional view taken along a line F—F in FIG. 8.

In the article 1A, the first fibrous nonwoven fabric layer f2 immediately underlies the panel 4 and the film f4 is joined only to the first fibrous nonwoven fabric layer f2 by means of the adhesive gin the zone where the panel 4 is present. Compared to the conventional article 1C (See FIG. 8) in which the film f7 immediately underlies the panel 22 and this film f7 is joined to the panel 22 and to the first fibrous nonwoven fabric layer f8 by means of the adhesive g with which the film's inner and outer surfaces are coated, the unique arrangement according to this invention as has been described just above improves the vapor-permeability of the article 1A and thereby allows moisture vapor to be smoothly exhausted from the interior to the exterior of the article 1A. In this way, it is not likely that the interior of the article 1A might be filled with moisture vapor and become stuffy.

The film f4 having the vapor-permeability of 2150–4000 g/m²·24 hrs immediately underlying the first fibrous nonwoven fabric layer f2 prevents body discharges from permeating the film f4 and there by prevents body discharges once retained within the article 1A from leaking out to the exterior of the article 1A even if body discharges such as urine, moisture contained in feces or menstrual discharge exude out through the first fibrous nonwoven fabric layer f2. In addition, the panel 4 and the first fibrous nonwoven fabric layer f2 are joined together. This arrangement reliably eliminates a possibility that the panel 4 might get out of its initial shape even if the wearer of the article 1A briskly moves.

In the article 1A, major parts of the end flaps 8 and the side flaps 9 are defined by the first and second fibrous nonwoven fabric layers f2, f3. This arrangement eliminates an anxiety that body discharges might permeate the end flaps 8 and the side flaps 9 even if body discharges exude out through the longitudinally opposite ends 4a and transversely opposite side edges 4b of the panel 4.

Figure 5:
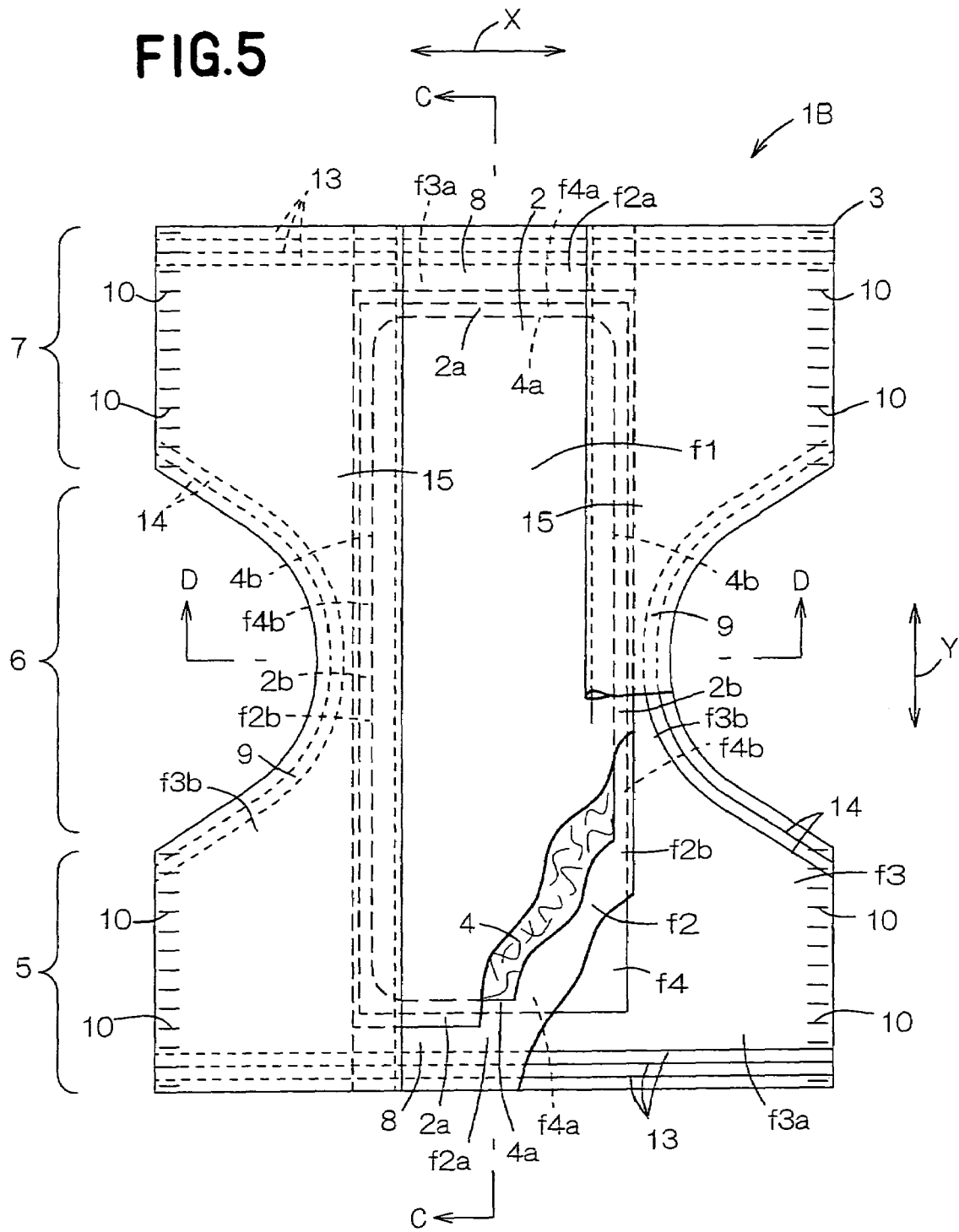
FIG. 5 is a partially cutaway developed plan view showing another embodiment of the article according to this invention.
Figure 6:
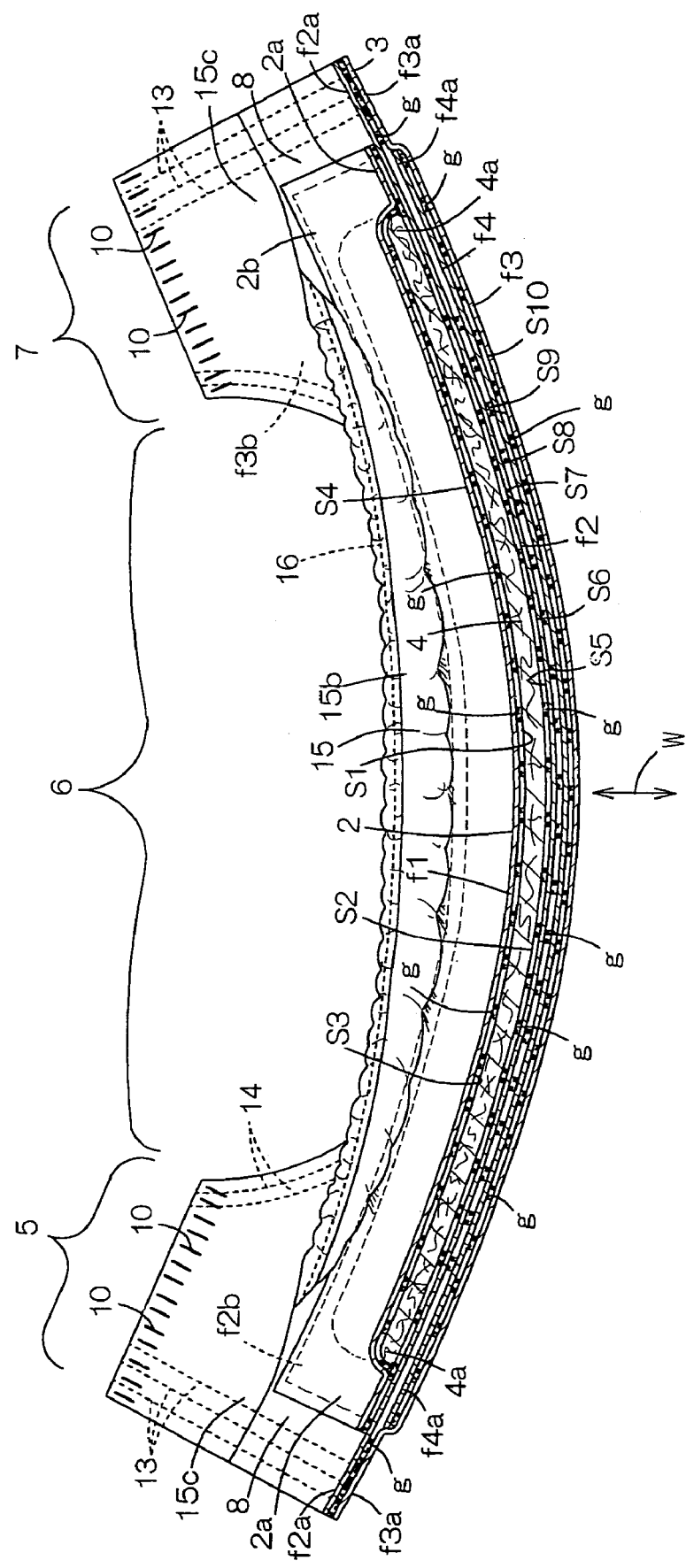
FIG. 6 is a sectional view taken along a line C—C in FIG. 5.
Figure 7:
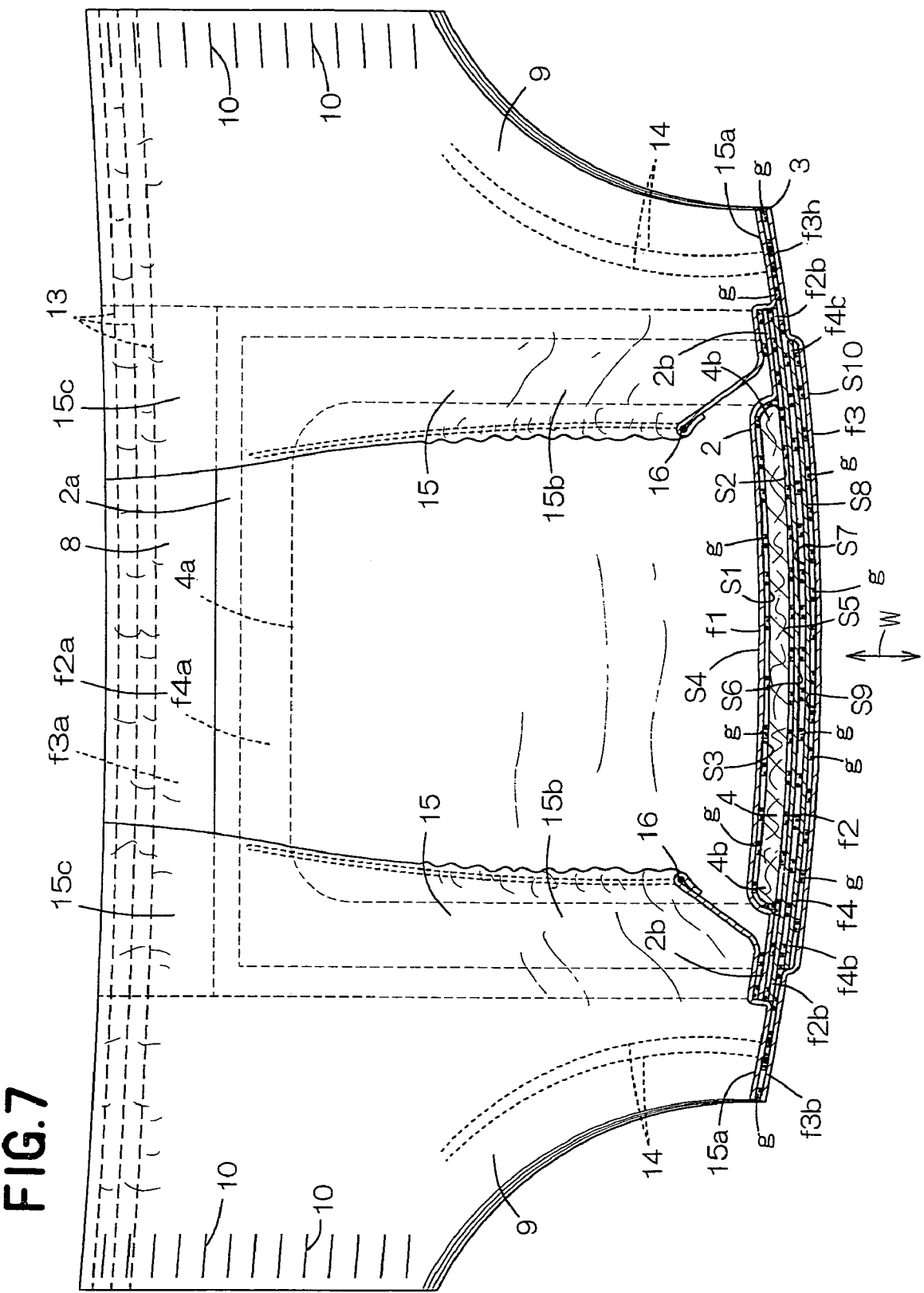
FIG. 7 is a sectional view taken along a line D—D in FIG. 5.

FIG. 5 is a partially cutaway developed plan view showing another embodiment 1B of the article according to this invention with front and rear waist regions 5, 7 having been disconnected from each other, and FIGS. 6 and 7 are sectional views taken along lines C—C and D—D, respectively, in FIG. 5 with the article 1B being slightly curved. In FIG. 5, a waist-circumferential direction is indicated by an arrow X and a longitudinal direction is indicated by an arrow Y. In FIGS. 6 and 7, a thickness direction is indicated by an arrow W.

Though not illustrates, the article 1B is of pull-on like the article 1A of FIG. 1 and the side flaps 9 of the front and rear waist regions 5, 7 are overlaid and joined together by means of a plurality of welding lines 10 arranged intermittently in the longitudinal direction so as to define a waist-hole and a pair of leg-holes.

The article 1B comprises a liquid-pervious topsheet 2, a substantially liquid-impervious backsheet 3 and a liquid-absorbent panel 4 interposed between the top- and back-sheets 2, 3. The article 1B is composed of a front waist region 5, a rear waist region 7 and a crotch region 6 extending between these waist regions 5, 7. The article 1B further includes a pair of end flaps 8 extending outside longitudinally opposite ends 4a of the panel 4 and a pair of side flaps 9 extending outside transversely opposite side edges 4b of the panel 4. A pair of leak-barrier sheets 15 are respectively attached to the side flaps 9 of the article 1B.

The end flaps 8 are respectively provided with a plurality of waist elastic members 13 extending in the waist-circumferential direction and contractibly attached thereto. In the crotch region 6, the side flaps 9 are respectively provided with a plurality of leg elastic members 14 extending in the leg-circumferential direction and contractibly attached thereto. The panel 4 extends over the crotch region 6 into the front and rear waist regions 5, 7. Components constituting the panel 4 are same as those of the panel 4 shown in FIG. 1.

The topsheet 2 is made of a breathable hydrophilic fibrous nonwoven fabric f1. The topsheet 2 is slightly larger than an upper surface S1 of the panel 4 and entirely covers the upper surface S1 of the panel 4. The topsheet 2 has its inner surface S3 intermittently joined to the upper surface S1 of the panel 4 by means of a hot melt adhesive g with which the topsheet 2 is coated.

The backsheet 3 comprises a breathable hydrophobic first fibrous nonwoven fabric layer f2, a breathable but hydrophobic second fibrous nonwoven fabric layer f3 and a breathable liquid-impervious plastic film f4. In the backsheet 3, the first fibrous nonwoven fabric layer f2 immediately underlies the panel 4, the film f4 immediately underlies the first fibrous nonwoven fabric layer f2 and the second fibrous nonwoven fabric layer f3 immediately underlies the film f4.

The first fibrous nonwoven fabric layers f2 and the film f4 are slightly larger than an under surface S2 of the panel 4 and cover the entire under surface S2 of the panel 4. The second fibrous nonwoven fabric layers f3 are larger than the first fibrous nonwoven fabric layer f2 and the film f4 and entirely covers the under surface S2 of the panel 4. The end flaps 8 are substantially defined by longitudinally opposite margins f2a, f3a of the first and second fibrous nonwoven fabric layers f2, f3, respectively. The side flaps 9 are substantially defined by transversely opposite margins f2b, f3b of the first and second fibrous nonwoven fabric layers f2, f3, respectively, and fixed lateral portions 15a of the leak-barrier sheets 15 which will be described later more in detail.

In the zone where the panel 4 is present, the first fibrous nonwoven fabric layer f2 has its inner surface S5 intermittently joined to the under surface S2 of the panel 4 by means of the hot melt adhesive g with which the first fibrous nonwoven fabric layer f2 is coated and the film f4 has its outer surface S8 intermittently joined to an inner surface S9 of the second fibrous nonwoven fabric layer f3 by means of the hot melt adhesive g with which the film f4 is coated. The adhesive g is intermittently applied substantially over whole areas of the inner surface S3 of the topsheet 2, the inner surface S5 of the nonwoven fabric layer f2 and the outer surface S8 of the film f4. The coating pattern for the adhesive g may be selected from spiral-, zigzag-, dot- and stripe-patterns.

In the zone of the crotch region 6 occupied by the panel 4, an inner surface S7 of the film f4 is intermittently joined to an outer surface S6 of the first fibrous nonwoven fabric layer f2 by means of the hot melt adhesive g with which the film f4 is coated. In the zone of the front and rear waist regions 5, 7 occupied by the panel 4, the outer surface S6 of the first fibrous nonwoven fabric layer f2 and the inner surface S7 of the film f4 are not joined together.

Each of the leak-barrier sheets 15 is made of a hydrophobic fibrous nonwoven fabric f5 and extends over the crotch region 6 into the front and rear waist regions 5, 7. The leak-barrier sheet 15 has a fixed lateral portion 15a secured to the associated side flap 9, a free lateral portion 15b normally biased to rise above the topsheet 2 and fixed longitudinally opposite end portions 15c collapsed inward in the waist-circumferential direction of the article 1B and fixed to the end flaps in such a collapsed state. The free lateral portion 15b is provided with an elastic member 16 extending in the longitudinal direction and contractibly attached thereto. The elastic member 16 is covered with a part of the free lateral portion 15b.

In the end flaps 8, the longitudinally opposite margins 2a of the topsheet 2 as well as the longitudinally opposite margins f4a of the film f4 extend outward slightly beyond the longitudinally opposite ends 4a of the panel 4 in the longitudinal direction and the longitudinally opposite margins f2a, f3a of the first and second fibrous nonwoven fabric layers f2, f3, respectively, extend further outward beyond the longitudinally opposite margins 2a, f4a in the longitudinal direction.

Along the longitudinally opposite margins 2a and the longitudinally opposite margins f2a, the respective inner surfaces S3, S5 of the topsheet 2 and the first fibrous nonwoven fabric layer f2, respectively, are intermittently joined together by means of the hot melt adhesive g. Along the longitudinally opposite margins f3a and the longitudinally opposite margins f4a, an inner surface S9 of the second fibrous nonwoven fabric layer f3 and an outer surface S8 of the film f4 are intermittently joined together by means of the hot melt adhesive g. Along the longitudinally opposite margins f2a and the longitudinally opposite margins f3a, the outer surface S6 of the first fibrous nonwoven fabric layer f2 and the inner surface S9 of the second fibrous nonwoven fabric layer f3 are intermittently joined together by means of the hot melt adhesive g.

The waist elastic members 13 are interposed between the longitudinally opposite margins f2a of the first fibrous nonwoven fabric layer f2 and the longitudinally opposite margins f3a of the second fibrous nonwoven fabric layer f3 and joined to the inner and outer surfaces S6, S9 of the nonwoven fabric layers f2, f3, respectively. The fixed longitudinal margins 15c of the respective leak-barrier sheets 15 are intermittently joined to the longitudinally opposite margins f2a of the first fibrous nonwoven fabric layer f2.

In the side flaps 9, the transversely opposite margins 2b of the topsheet 2 as well as the transversely opposite margins f2b of the first fibrous nonwoven fabric layer f2 and transversely opposite margins f4a of the film f4 extend outward slightly beyond the transversely opposite side edges 4b of the panel 4 in the waist-circumferential direction and the transversely opposite margins f3b, the fixed lateral portions 15a of the leak-barrier sheets 15 extend further outward beyond the transversely opposite margins 2b, f2b, f4b in the waist-circumferential direction.

Along the transversely opposite margins 2b and the transversely opposite margins f2b, the respective inner surfaces S3, S5 of the topsheet 2 and the first fibrous nonwoven fabric layer f2 are intermittently joined together by means of the hot melt adhesive g. Along the transversely opposite margins f2b and the transversely opposite margins f4b, the outer surface S6 of the first fibrous nonwoven fabric layer f2 and the inner surface S7 of the film f4 are intermittently joined together by means of the hot melt adhesive g.

The leg elastic members 14 are interposed between the transversely opposite margins f3b of the second fibrous nonwoven fabric layer f3 and the fixed lateral portions 15a of the leak-barrier sheets 15 and secured to the respective inner surfaces S9 of the transversely opposite margins f3b and the fixed lateral portions 15a. The fixed lateral portions 15a of the leak-barrier sheets 15 are intermittently secured to the transversely opposite margins 2b of the topsheet 2 and to the transversely opposite margins f3b of the second fibrous nonwoven fabric layer f3 by means of the hot melt adhesive g.

In the zone where the panel 4 is present, an amount of the adhesive with which the first fibrous nonwoven fabric layer f2 and the film f4 are coated is in the same range as described with reference to FIG. 1. The vapor-permeability of the film f4 and the basis weight of the topsheet 2, the first fibrous nonwoven fabric layer f2, the second fibrous nonwoven fabric layer f3 and the film f4 are also same as in the case of FIG. 1.

In the article 1B, the front and rear waist regions 5, 7 exhibit a vapor-permeability in a range of 2000–3800 $g/m^2 \cdot 24$ hrs. Like the case of FIG. 1, such a vapor-permeability is the value as measured using the same method as in the case of FIG. 1 in the thickness direction of the article 1B without the topsheet 2 in the zone where the panel 4 is present.

In the front and rear waist regions 5, 7 of the article 1B, the first fibrous nonwoven fabric layer f2 underlies the panel 4 and the film f4 is bonded to the second fibrous nonwoven fabric layer f3 by means of the adhesive g only in the zone where the panel 4 is present. Compared to the conventional article 1C (See FIG. 8) in which the film f7 immediately underlies the panel 22 and the film f7 is joined to the panel 22 and to the first fibrous nonwoven fabric layer f8 by means of the adhesive g with which the inner and outer surfaces of the film 7 are coated, the unique arrangement according to this invention as has been described just above improves the vapor-permeability of the article 1B and thereby allows moisture vapor generated in the front and rear waist regions 5, 7 to be smoothly exhausted from the interior to the exterior of the article 1B. In this way, it is not likely that the interior of the article 1B might be filled with moisture vapor and become stuffy.

The film f4 having the vapor-permeability of 2150–4000 $g/m^2 \cdot 24$ hrs immediately underlying the first fibrous nonwoven fabric layer f2 prevents body discharges from permeating the film f4 and thereby prevents body discharges once retained within the article 1B from leaking out to the exterior of the article 1B even if body discharges exude out through the first fibrous nonwoven fabric layer f2. In addition, the panel 4 and the first fibrous nonwoven fabric layer f2 are joined together. This arrangement reliably eliminates a possibility that the panel 4 might get out of its initial shape even if the wearer of the article 1B briskly moves.

In the zone of the crotch region 6 occupied by the panel 4, the film f4 is joined to the first fibrous nonwoven fabric f2 by means of the adhesive g so that the panel 4, the first and second fibrous nonwoven fabric layers f2, f3 and the film f4 may be integrated together. Such arrangement elimi-nates an anxiety that the film f4 might be moved with respect to the panel 4 and ensures that the film f4 reliably prevent leakage of body discharges.

In the article 1B, major part of the end flaps 8 is formed by the first and second fibrous nonwoven fabric layers f2, f3 and major part of the side flaps 9 is formed by the second fibrous nonwoven fabric layers f3 and the leak-barrier sheets 15. This arrangement eliminates an anxiety that body discharges might permeate the end flaps 8 and the side flaps 9 even if body discharges exude out through the longitudinally opposite ends 4a and transversely opposite side edges 4b of the panel 4.

In the article 1B, the free lateral portions 15b of the respective leak-barrier sheets 15 rise above the topsheet 2 and form barriers against body discharges as the elastic members 16 contract. Any leakage of bodily discharges from the crotch region 6 can be thereby prevented.

The top sheet 2 may be made of, in addition to the hydrophilic fibrous nonwoven fabric, a hydrophobic fibrous nonwoven fabric having a plurality of perforations or a liquid-pervious plastic film having a plurality of fine perforations. The leak-barrier sheet 15 may be made of, in addition to the hydrophobic fibrous nonwoven fabric, a liquid-impervious plastic film or a composite sheet comprising a hydrophobic fibrous nonwoven fabric and a liquid-impervious plastic film laminated to each other.

The nonwoven fabric may be selected from the group including products obtained by spun lace-, needle punch-, melt brown-, thermal bond-, spun bond-, chemical bond- and air-through-processes. Component fibers of the nonwoven fabric may be selected from the group including of polyolefin-, polyester- and polyamide-based fibers and core-and-sheath type or side-by-side type conjugated fiber of polyethylene/polypropylene or polyethylene/polyester.

The hot melt adhesive may be of the well known art such as a styrene- or olefin-based hot melt adhesive.

This invention is applicable not only the pull-on disposable wearing article 1A, 1B with the front and rear waist regions previously connected to each other but also to the open-type disposable wearing article with the front and rear waist regions adapted to be connected to each other in the course of actually putting the article on a wearer's body.

As will be apparent from the foregoing description, with the disposable wearing article according to this invention, the first fibrous nonwoven fabric layer immediately underlies the panel, the first fibrous nonwoven fabric layer is intermittently joined to the panel by means of the hot melt adhesive applied to the first fibrous nonwoven fabric layer and, in the zone occupied by the panel, the breathable but liquid-impervious film is intermittently joined to the first fibrous nonwoven fabric layer or the second fibrous nonwoven fabric layer by means of the hot melt adhesive applied onto the film. Compared to the conventional article in which the inner and outer surfaces of the film are coated with the adhesive, the arrangement according to this invention as has been described just above improves the vapor-permeability of the article and allows vapor to be smoothly let out from the interior to the exterior of the article. With the article put on the wearer's body, there is no apprehension that vapor staying within the article might cause uncomfortable stuffiness within the article.

In this article, the film immediately underlying the first fibrous nonwoven fabric layer serves to prevent body discharges from leaking into the exterior of the article even if body discharges once absorbed by the panel exude through the first fibrous nonwoven fabric, since body discharges can not permeate the film. Furthermore, the feature that the panel and the first fibrous nonwoven fabric layer are joined together advantageously eliminates an anxiety that the panel might get out of its initial shape even if the article wearer briskly moves.

The vapor-permeability in the thickness direction of the article without the topsheet is in the range of 2000–3800 g/m²·24 hrs as measured in the zone occupied by the panel. Thus the article according to this invention exhibits an improved vapor-permeability compared to the conventional article.

In the article in which the amount of the hot melt adhesive with which the first fibrous nonwoven fabric layer and the film are coated in the zone occupied by the panel is in the range of 1–10 g/m², it is possible to maintain a sufficient joining force to avoid the apprehension that the first fibrous nonwoven fabric layer might be unintentionally peeled off from the panel and/or the film might be unintentionally peeled off from the first fibrous nonwoven fabric layer or the second fibrous nonwoven fabric layer. In addition, there is no possibility that the vapor-permeability of the first fibrous nonwoven fabric layer and the film might be deteriorated due to the presence of the adhesive.

In the article in which the major parts of the end flaps and the side flaps, respectively, are defined by the first and second fibrous nonwoven fabric layers and the film, at least by the second fibrous nonwoven fabric layer, these flaps are substantially liquid-impervious and there is no possibility that body discharges might exude through the end flaps and the side flaps even if body discharges exude out beyond the longitudinally opposite ends and the transversely opposite side edges of the panel.

What is claimed is:

1. A disposable wearing article comprising:
   a liquid-pervious topsheet facing a wearer's body;
   a liquid-impervious backsheet adapted to face a wearer's body;
   a liquid-absorbent panel interposed between said topsheet and backsheets;
   a pair of end flaps extending outside longitudinally opposite ends of said panel; and
   a pair of side flaps extending outside transversely opposite side edges of said panel;
   wherein said backsheet comprises:
   a breathable but hydrophobic first fibrous nonwoven fabric layer underlying said panel and covering at least an entire under surface of said panel,
   a breathable but liquid-impervious plastic film underlying said first fibrous nonwoven fabric and covering at least said entire under surface of said panel, and
   a breathable but hydrophobic second fibrous nonwoven fabric layer underlying said film and being larger than said film; and
   wherein, in a zone occupied by said panal, said first fibrous nonwoven fabric layer is intermittently joined to said lower surface of said panel by hot melt adhesive and said film is intermittently joined to one of said first fibrous nonwoven fabric layer and said second fibrous nonwoven fabric layer by hot melt adhesive wherein, in said zone occupied by said panel, said article without said topsheet exhibits a vapor-permeability in a thickness direction of 2000–3800 g/m²·24 hrs.;
   said film exhibits a vapor-permeability in a thickness direction of 2150–4000g/m²·24 hrs.;
   in said zone occupied by said panel, said first fibrous nonwoven fabric layer and said film are coated with an amount of said adhesive in a range of 1–10 g/m²;
   in the zone occupied by said panel, film is disposed between said first and second fibrous nonwoven fabric layers, said fiilm is intermittently joined only to said first fibrous nonwoven fabric layer, and said film is not joined to said second fibrous nonwoven fabric layer.

2. The wearing article according to claim 1, wherein
   major parts of said end flaps and said side flaps are defined at least by said second fibrous nonwoven fabric layer, and
   in said end flaps and said side flaps, said topsheet is intermittently joined at least to said first fibrous nonwoven fabric layer, and said first fibrous nonwoven fabric layer and said second fibrous nonwoven fabric layer are intermittently joined together.

3. The wearing article according to claim 1, wherein said topsheet is made of a breathable and hydrophilic fibrous nonwoven fabric and intermittently joined to an upper sufface of said panel by adhesive.

4. The wearing article according to claim 1, wherein
   the first and second fibrous non-woven fabric layers are larger than said film and respectively cover entire upper and lower surfaces of said film; and
   the first and second fibrous non-woven fabric layers are bonded together only in regions located outside a boundary of said film.

5. The wearing article according to claim 4, wherein the first and second fibrous non-woven fabric layers have about the same size.

6. The wearing article according to claim 1, wherein
   the first and second fibrous non-woven fabric layers are larger than said film and respectively cover entire upper and lower surfaces of said film; and
   the first and second fibrous non-woven fabric layers have portions extending outwardly beyond a periphery of said film and being bonded directly to each other.

* * * * *